United States Patent [19]

Seele et al.

[11] Patent Number: 5,250,555
[45] Date of Patent: Oct. 5, 1993

[54] 1-HALO-1-AZOLYLMETHANE DERIVATIVES AND FUNGICIDES CONTAINING THESE

[75] Inventors: Rainer Seele, Fussgoenheim; Norbert Goetz, Worms; Thomas Saupe, Sandhausen; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 763,812

[22] Filed: Sep. 23, 1991

[30] Foreign Application Priority Data

Oct. 29, 1990 [DE] Fed. Rep. of Germany ....... 4034352

[51] Int. Cl.$^5$ ................. A01N 43/653; C07D 249/08
[52] U.S. Cl. .................... 514/383; 514/184; 548/101; 548/262.2; 548/267.2; 548/267.8; 548/268.2; 548/268.6
[58] Field of Search ............... 574/383, 184; 548/101, 548/262.2, 267.2, 267.8, 268.2, 268.6

[56] References Cited

U.S. PATENT DOCUMENTS 4,657,921  4/1987  Frick et al. ................... 514/383
4,960,782 10/1990  Gyvner et al. ................ 514/383

Primary Examiner—Patricia L. Morris
Attorney, Agent, or Firm—Oblon, Spivak, McClelland, Maier & Neustadt

[57] ABSTRACT

1-Halo-1-azolylmethane derivatives of the formula

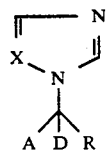

where
A and R are each alkyl, benzyl, benzoyl, acyl, biphenylyl, naphthyl, hetaryl or phenyl, it being possible for each of these radicals to be substituted;
D is Cl or Br,
X is CH or N,
and their plant-compatible acid addition salts and metal complexes are used as fungicides.

8 Claims, No Drawings

1-HALO-1-AZOLYLMETHANE DERIVATIVES AND FUNGICIDES CONTAINING THESE

The present invention relates to novel 1-halo-1-azolylmethane derivatives, to fungicides containing these, to processes for the preparation thereof and to the use thereof as fungicides. The novel compounds have a good fungicidal action.

The use of 1-halo-1-azolylmethane derivatives as fungicides has been disclosed (EP 346 727). However, their action is unsatisfactory.

We have now found that 1-halo-1-azolylmethane derivatives of the formula I

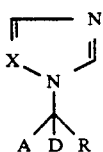

where
A and R are identical or different and are each $C_1$–$C_8$-alkyl, $C_3$–$C_8$-cycloalkyl, benzyl, benzoyl, $C_1$–$C_8$-acyl, biphenylyl, naphthyl, hetaryl or phenyl, it being possible for each of these radicals to be substituted once to three times by halogen, nitro, phenoxy, amino, $C_1$–$C_4$-alkyl, $C_1$–$C_4$-alkoxy or $C_1$–$C_4$-haloalkyl;
D is Cl or Br,
X is CH or N,
and the plant-compatible acid addition salts or metal complexes thereof, have a better fungicidal action than known azole compounds.

Examples of specific meanings of the substituents in the formula I are the following: A and R independently of one another unbranched or branched $C_1$–$C_8$-alkyl, especially $C_1$–$C_4$-alkyl such as methyl, ethyl, propyl, isopropyl, butyl, iso-butyl, sec-butyl or tert-butyl, $C_3$–$C_8$-cycloalkyl such as cyclopropyl, cyclopentyl, cyclohexyl, benzyl and halobenzyl such as 2-chlorobenzyl, 3-chlorobenzyl, 4-chlorobenzyl, 2-fluorobenzyl, 3-fluorobenzyl, 4-fluorobenzyl and 2-bromobenzyl, 3-bromobenzyl and 4-bromobenzyl, 2,3-dichlorobenzyl, 2,4-dichlorobenzyl, 2,5-dichlorobenzyl and 2,6-dichlorobenzyl;

benzyl monosubstituted by nitro, phenoxy, amino or $C_1$–$C_4$-alkyl, such as 4-nitrobenzyl, 4-phenoxybenzyl, 4-aminobenzyl and 4-methylbenzyl, 4-isopropylbenzyl and 4-tert-butylbenzyl;

benzyl substituted once or twice by $C_1$–$C_4$-alkoxy, such as 2-methoxybenzyl, 3-methoxybenzyl, 4-methoxybenzyl, 4-tert-butyloxybenzyl and 2,4-dimethoxybenzyl;

trihalomethylbenzyl such as 2-trifluoromethylbenzyl, 3-trifluoromethylbenzyl and 4-trifluoromethylbenzyl;

benzoyl and halobenzoyl such as 2-chlorobenzoyl, 3-chlorobenzoyl, 4-chlorobenzoyl, 2-fluorobenzoyl, 4-fluorobenzoyl and 2-bromobenzoyl, 3-bromobenzoyl and 4-bromobenzoyl, 2,3-dichlorobenzoyl, 2,4-dichlorobenzoyl and 2,5-dichlorobenzoyl;

benzoyl monosubstituted by nitro, phenoxy, amino or $C_1$–$C_4$-alkyl, such as 4-nitrobenzoyl, 4-phenoxybenzoyl, 4-aminobenzoyl and 4-methylbenzoyl;

benzoyl substituted once or twice by $C_1$–$C_4$-alkoxy, such as 2-methoxybenzoyl, 3-methoxybenzoyl, 4-methoxybenzoyl and 2,4-dimethoxybenzoyl;

trihalomethylbenzoyl such as 2-trifluoromethylbenzoyl, 3-trifluoromethylbenzoyl and 4-trifluoromethylbenzoyl;

naphthyl such as 1-naphthyl and 2-naphthyl;

biphenylyl such as o-, m- or p-biphenylyl;

phenyl and halophenyl such as 2-chlorophenyl, 3-chlorophenyl, 4-chlorophenyl, 2-fluorophenyl, 3-fluorophenyl, 4-fluorophenyl and 2-bromophenyl, 3-bromophenyl and 4-bromophenyl, 2,3-dichlorophenyl, 2,4-dichlorophenyl, 2,5-dichlorophenyl and 2,6-dichlorophenyl;

phenyl monosubstituted by nitro, phenoxy, amino or $C_1$–$C_4$-alkyl, such as 3-nitrophenyl, 4-nitrophenyl, 3-phenoxyphenyl, 4-phenoxyphenyl, 3-aminophenyl and 4-aminophenyl, and 4-methylphenyl, 4-isopropylphenyl and 4-tert-butylphenyl;

phenyl substituted once or twice by $C_1$–$C_4$-alkoxy, such as 2-methoxyphenyl, 3-methoxyphenyl, 4-methoxyphenyl, 4-tert-butyloxyphenyl and 2,3-dimethoxyphenyl, and 2,4-dimethoxyphenyl;

trihalomethylphenyl such as 2-trifluoromethyl-, 3-trifluoromethyl- and 4-trifluoromethylphenyl;

5- or 6-membered hetaryl such as 2-pyrrolyl, 3-pyrrolyl, 2-furyl, 2-thienyl, 3-thienyl, 2-pyridyl, 3-pyridyl, 4-pyridyl, 1,3-dioazol-2-yl, 4-oxazolyl, 5-oxazolyl, 3-isoxazolyl, 4-isoxazolyl, 5-isoxazolyl, 4-thiazolyl and 5-thiazolyl;

$C_1$–$C_8$-acyl such as $C_1$–$C_4$-alkylcarbonyl such as acetyl or propionyl.

The compounds of the formula I contain asymmetric carbon atoms and can therefore exist as enantiomers and diastereomers. The invention embraces both the pure isomers and the mixtures thereof. The mixtures of diastereomers can be separated into the components by conventional methods, eg. by fractional crystallization or by chromatography on silica gel. The racemates of the novel compounds can be resolved by conventional methods, for example by salt formation with an optically active acid, separation of the diastereomeric salts and liberation of the enantiomers with a base.

Both the individual diastereomers or enantiomers and mixtures thereof can be used as fungicidal active ingredients.

Examples of acid addition salts are the hydrochlorides, bromides, sulfates, nitrates, phosphates, oxalates or dodecylbenzenesulfonates. The activity of the salts depends on the cation so that the anion is generally immaterial. The novel active ingredient salts are prepared by reacting the 1-halo-1-azolylmethane derivatives with acids.

Metal complexes of the active ingredients I or their salts can be formed, for example, with copper, zinc, tin, manganese, iron, cobalt or nickel by reacting the 1-halo-1-azolylmethane derivatives with the appropriate metal salts.

The novel compounds I are prepared in a very advantageous manner by methods similar to that described by H. Matsumoto et al. (Tetrahedron Letters 52 (1979) 5011) by reacting a ketone of the formula II with an azole of the formula III and an acid halide ($YD_2$) as shown in the following equation:

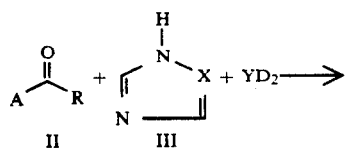

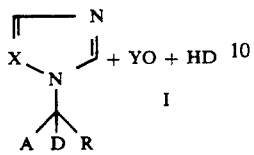

The inorganic acid halides (YD$_2$) are halogenating agents such as phosphorus oxychloride, thiophosgene, preferably phosgene, and thionyl chloride and bromide.

The acid halide is preferably employed in not less than equimolar amounts based on the ketone II. The azole component III is employed, for example, in more than twice, preferably 5-6 times, the molar amount based on the acid chloride or bromide.

The reaction is preferably carried out at from $-30°$ to $+100°$ C., particularly preferably from $0°$ to $20°$ C., in the presence of a solvent.

Examples of preferred solvents are nitriles such as acetonitrile, ethers such as tetrahydrofuran, diethyl ether or dioxane. Particularly preferred solvents are hydrocarbons and chlorohydrocarbons such as hexane, benzene, toluene, methylene chloride, tetrachloromethane or mixtures thereof.

The reaction is generally carried out under atmospheric pressure unless a higher pressure, up to about 5 bar, is advisable because of the volatility of a reactant.

Since the acid halides and the intermediates are sensitive to hydrolysis, the operations are preferably carried out with exclusion of moisture, particularly preferably under a protective gas atmosphere.

The Example which follows illustrates the preparation of the active ingredients.

Preparation Example

EXAMPLE 1

1,3-Diphenyl-2-chloro-2-(1,2,4-triazol-1-yl)propane

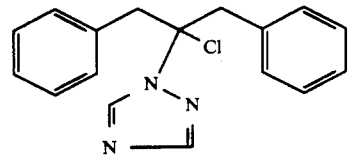

42.7 g (0.39 mol) of thionyl chloride were added to a solution of 98.6 g (1.43 mol) of triazole in 250 ml of methylene chloride under a nitrogen atmosphere at 0° C. and, after stirring at 25° C. for 30 minutes, 50 g (0.24 mol) of diphenylacetone were added.

After the reaction had taken place at 25° C. for 12 hours, 200 ml of water were added, and the aqueous phase was separated off and extracted twice with methylene chloride. The combined organic phases were then worked up in a conventional manner to give the triazole derivative.

Yield: 56.4 g (79%)

Melting point: 100° to 102° C.

The compounds listed in the Table can be prepared in a similar manner to Example 1.

TABLE

| Ex. | A | R | D | X | M.p./IR |
|---|---|---|---|---|---|
| 1 | CH$_2$C$_6$H$_5$ | —CH$_2$C$_6$H$_5$ | Cl | N | 100-102° C. |
| 2 | CH$_2$C$_6$H$_5$ | CH$_3$ | Cl | N | |
| 3 | CH$_2$C$_6$H$_5$ | C$_3$H$_7$ | Cl | N | |
| 4 | CH$_2$C$_6$H$_5$ | Cyclohexyl | Cl | N | |
| 5 | CH$_2$C$_6$H$_5$ | —CH$_2$—C$_6$H$_4$—Cl | Cl | N | |
| 6 | CH$_2$C$_6$H$_5$ | —CH$_2$—C$_6$H$_4$—F | Cl | N | |
| 7 | CH$_2$C$_6$H$_5$ | —CH$_2$—C$_6$H$_4$(o-Cl) | Cl | N | |
| 8 | CH$_2$C$_6$H$_5$ | —C(O)—C$_6$H$_4$—F | Cl | N | |

TABLE-continued structure:
```
    ╱═╲N
   ‖   ‖
  X    ╱
   ╲N═╱
    │
   C
  ╱│╲
 A D R
```

| Ex. | A | R | D | X | M.p./IR |
|---|---|---|---|---|---|
| 9 | CH$_2$C$_6$H$_5$ | —CO—C$_6$H$_4$—Cl (4-) | Cl | N | |
| 10 | CH$_2$C$_6$H$_5$ | —CO—CH$_3$ | | | |
| 11 | CH$_2$C$_6$H$_5$ | —CO—C$_3$H$_7$ | Cl | N | |
| 12 | CH$_2$C$_6$H$_5$ | 4-Biphenylyl | Cl | N | |
| 13 | CH$_2$C$_6$H$_5$ | 1-Naphthyl | Cl | N | |
| 14 | CH$_2$C$_6$H$_5$ | C$_6$H$_5$ | Cl | N | |
| 15 | CH$_2$C$_6$H$_5$ | 2-Cl-C$_6$H$_4$ | Cl | N | |
| 16 | CH$_2$C$_6$H$_5$ | 4-Cl—C$_6$H$_4$ | Cl | N | |
| 17 | CH$_2$C$_6$H$_5$ | 2,4-Cl$_2$—C$_6$H$_3$ | Cl | N | |
| 18 | CH$_2$C$_6$H$_5$ | 2-F—C$_6$H$_4$ | Cl | N | |
| 19 | CH$_2$C$_6$H$_5$ | 4-F—C$_6$H$_4$ | Cl | N | |
| 20 | CH$_2$C$_6$H$_5$ | 4-CH$_3$—C$_6$H$_4$ | Cl | N | |
| 21 | CH$_2$C$_6$H$_5$ | 4-OCH$_3$—C$_6$H$_4$ | Cl | N | |
| 22 | CH$_2$C$_6$H$_5$ | 2-CF$_3$—C$_6$H$_4$ | Cl | N | |
| 23 | CH$_2$—C$_6$H$_4$—F (4-) | CH$_3$ | Cl | N | |
| 24 | CH$_2$—C$_6$H$_4$—F (4-) | C$_3$H$_7$ | Cl | N | |
| 25 | CH$_2$—C$_6$H$_4$—F (4-) | C$_4$H$_9$ | Cl | N | |
| 26 | CH$_2$—C$_6$H$_4$—F (4-) | Cyclohexyl | Cl | N | |
| 27 | CH$_2$—C$_6$H$_4$—F (4-) | —CH$_2$—C$_6$H$_5$ | Cl | N | |
| 28 | CH$_2$—C$_6$H$_4$—F (4-) | —CH$_2$—C$_6$H$_4$—F (4-) | Cl | N | 150° C. |
| 29 | CH$_2$—C$_6$H$_4$—F (4-) | —CH$_2$—C$_6$H$_4$—F (4-) | Cl | CH | |
| 30 | CH$_2$—C$_6$H$_4$—F (4-) | —CH$_2$—C$_6$H$_4$—F (2-) | Cl | N | Resin |

TABLE-continued
| Ex. | A | R | D | X | M.p./IR |
|---|---|---|---|---|---|
| 31 | 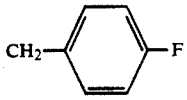 CH₂–C₆H₄–F | –CH₂–C₆H₄–Cl | Cl | N | |
| 32 | 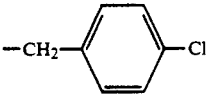 CH₂–C₆H₄–F | –CO–C₆H₅ | Cl | N | |
| 33 | 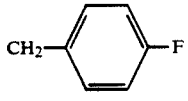 CH₂–C₆H₄–F | –CO–C₆H₄–F | Cl | N | |
| 34 | 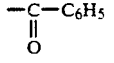 CH₂–C₆H₄–F | –CO–C₆H₄–Cl | Cl | N | |
| 35 | 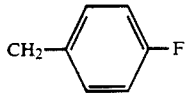 CH₂–C₆H₄–F | –CO–CH₃ | Cl | N | |
| 36 | 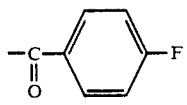 CH₂–C₆H₄–F | –CO–C₃H₇ | Cl | N | |
| 37 | 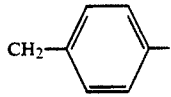 CH₂–C₆H₄–F | 4-Biphenylyl | Cl | N | |
| 38 | 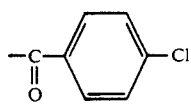 CH₂–C₆H₄–F | 1-Naphthyl | Cl | N | |
| 39 | 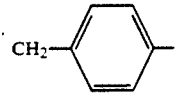 CH₂–C₆H₄–F | C₆H₅ | Cl | N | |
| 40 | 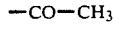 CH₂–C₆H₄–F | 2-Cl–C₆H₄ | Cl | N | |
| 41 | 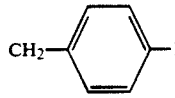 CH₂–C₆H₄–F | 4-Cl–C₆H₄ | Cl | N | |
| 42 | 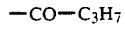 CH₂–C₆H₄–F | 2,4-Cl₂–C₆H₃ | Cl | N | |

TABLE-continued
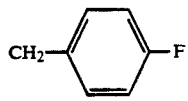
| Ex. | A | R | D | X | M.p./IR |
|---|---|---|---|---|---|
| 43 | CH₂-C₆H₄-F (4-F) | 2-F—C₆H₄ | Cl | N | |
| 44 | CH₂-C₆H₄-F (4-F) | 4-F—C₆H₄ | Cl | N | |
| 45 | CH₂-C₆H₄-F (4-F) | 4-CH₃—C₆H₄ | Cl | N | |
| 46 | CH₂-C₆H₄-F (4-F) | 4-OCH₃—C₆H₄ | Cl | N | |
| 47 | CH₂-C₆H₄-F (4-F) | 4-CF₃—C₆H₄ | Cl | N | |
| 48 | CH₂-C₆H₄-F (4-F) | 2-Furyl | Cl | N | |
| 49 | CH₂-C₆H₄-Cl (4-Cl) | CH₃ | Cl | N | |
| 50 | CH₂-C₆H₄-Cl (4-Cl) | C₃H₇ | Cl | N | |
| 51 | CH₂-C₆H₄-Cl (4-Cl) | —CH₂-C₆H₄-Cl (4-Cl) | Cl | N | |
| 52 | CH₂-C₆H₄-Cl (4-Cl) | —CO-C₆H₄-F (4-F) | Cl | N | |
| 53 | CH₂-C₆H₄-Cl (4-Cl) | —CO-C₆H₄-Cl (4-Cl) | Cl | N | |
| 54 | CH₂-C₆H₄-Cl (4-Cl) | —CO—CH₃ | Cl | N | |

TABLE-continued
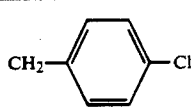
| Ex. | A | R | D | X | M.p./IR |
|---|---|---|---|---|---|
| 55 | 4-Cl-C6H4-CH2- | —CO—C3H7 | Cl | N | |
| 56 | 4-Cl-C6H4-CH2- | C6H5 | Cl | N | |
| 57 | 4-Cl-C6H4-CH2- | 4-Cl—C6H4 | Cl | N | |
| 58 | 4-Cl-C6H4-CH2- | 4-F-C6H4 | Cl | N | |
| 59 | 4-Cl-C6H4-CH2- | 2,4-Cl2—C6H3 | Cl | N | |
| 60 | 2,4-Cl2-C6H3-CH2- | CH3 | Cl | N | |
| 61 | 2,4-Cl2-C6H3-CH2- | C4H9 | Cl | N | 2960, 1588, 1475, 1280 cm$^{-1}$ |
| 62 | 2,4-Cl2-C6H3-CH2- | CH2—C6H5 | Cl | N | |
| 63 | 2,4-Cl2-C6H3-CH2- | —CH2-C6H4-4-Cl | Cl | N | |
| 64 | 2,4-Cl2-C6H3-CH2- | —CH2-C6H4-4-F | Cl | N | |
| 65 | 2,4-Cl2-C6H3-CH2- | —CH2-C6H3-2,4-Cl2 | Cl | N | |

TABLE-continued
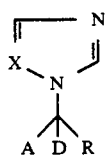
| Ex. | A | R | D | X | M.p./IR |
|---|---|---|---|---|---|
| 66 | 2,4-Cl₂-C₆H₃-CH₂ | -CO-C₆H₄-4-Cl | Cl | N | |
| 67 | 2,4-Cl₂-C₆H₃-CH₂ | -CO-C₆H₄-4-F | Cl | N | |
| 68 | 2,4-Cl₂-C₆H₃-CH₂ | —CO—CH₃ | Cl | N | |
| 69 | 2,4-Cl₂-C₆H₃-CH₂ | —CO—C₄H₉ | Cl | N | |
| 70 | 2,4-Cl₂-C₆H₃-CH₂ | C₆H₅ | Cl | N | |
| 71 | 2,4-Cl₂-C₆H₃-CH₂ | 4-Cl—C₆H₄ | Cl | N | |
| 72 | 2,4-Cl₂-C₆H₃-CH₂ | 2-Cl—C₆H₄ | Cl | N | |
| 73 | 2,4-Cl₂-C₆H₃-CH₂ | 2,4-Cl₂—C₆H₃ | Cl | N | |
| 74 | 2,4-Cl₂-C₆H₃-CH₂ | 4-F—C₆H₄ | Cl | N | |
| 75 | 2,4-Cl₂-C₆H₃-CH₂ | 4-CH₃—C₆H₄ | Cl | N | |

TABLE-continued $$\begin{array}{c} \text{structure with imidazole ring, X-N, A-D-R substituents} \end{array}$$

| Ex. | A | R | D | X | M.p./IR |
|---|---|---|---|---|---|
| 76 | 2,4-Cl₂-C₆H₃-CH₂- | 4-CF₃—C₆H₄ | Cl | N | |
| 77 | 2,4-Cl₂-C₆H₃-CH₂- | Cyclohexyl | Cl | N | |
| 78 | —C(O)—C₆H₅ | CH₃ | Cl | N | |
| 79 | —C(O)—C₆H₅ | C₃H₇ | Cl | N | |
| 80 | —C(O)—C₆H₅ | C₄H₉ | Cl | N | |
| 81 | —C(O)—C₆H₅ | Cyclohexyl | Cl | N | |
| 82 | —C(O)—C₆H₅ | C₆H₅ | Cl | N | 1698, 1502, 1447, 1231, 743 cm⁻¹ |
| 83 | —C(O)—C₆H₅ | 2-Cl—C₆H₄ | Cl | N | |
| 84 | —C(O)—C₆H₅ | 4-Cl—C₆H₄ | Cl | N | |
| 85 | —C(O)—C₆H₅ | 2,4-Cl₂—C₆H₃ | Cl | N | |
| 86 | —C(O)—C₆H₅ | 2-F—C₆H₄ | Cl | N | |
| 87 | —C(O)—C₆H₅ | 4-F—C₆H₄ | Cl | N | |
| 88 | —C(O)—C₆H₅ | 2-Br—C₆H₄ | Cl | N | |
| 89 | —C(O)—C₆H₅ | 2-CH₃—C₆H₄ | Cl | N | |
| 90 | —C(O)—C₆H₅ | 4-CH₃—C₆H₄ | Cl | N | |
| 91 | —C(O)—C₆H₅ | 2-CF₃—C₆H₄ | Cl | N | |

TABLE-continued

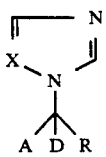

| Ex. | A | R | D | X | M.p./IR |
|---|---|---|---|---|---|
| 92 | −C(=O)−C₆H₅ | 4-CF₃−C₆H₄ | Cl | N | |
| 93 | −C(=O)−C₆H₅ | 4-OCH₃−C₆H₄ | Cl | N | |
| 94 | −C(=O)−C₆H₅ | 1-Naphthyl | Cl | N | |
| 95 | −C(=O)−C₆H₅ | 2-Naphthyl | Cl | N | |
| 96 | −C(=O)−C₆H₅ | 4-Biphenylyl | Cl | N | |
| 97 | −C(=O)−C₆H₅ | 2-Thienyl | Cl | N | |
| 98 | −C(=O)−C₆H₅ | 3-Thienyl | Cl | N | |
| 99 | −C(=O)−C₆H₅ | 2-Pyridyl | Cl | N | |
| 100 | −C(=O)−C₆H₅ | 3-Pyridyl | Cl | N | |
| 101 | −C(=O)−C₆H₅ | 4-Pyridyl | Cl | N | |
| 102 | −C(=O)−C₆H₄−4-Cl | CH₃ | Cl | N | |
| 103 | −C(=O)−C₆H₄−4-Cl | C₃H₇ | Cl | N | |
| 104 | −C(=O)−C₆H₄−4-Cl | C₄H₉ | Cl | N | |
| 105 | −C(=O)−C₆H₄−4-Cl | Cyclohexyl | Cl | N | |
| 106 | −C(=O)−C₆H₄−4-Cl | C₆H₅ | Cl | N | |

TABLE-continued
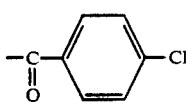
| Ex. | A | R | D | X | M.p./IR |
|---|---|---|---|---|---|
| 107 | 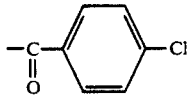 | 2-Cl—$C_6H_4$ | Cl | N | |
| 108 | 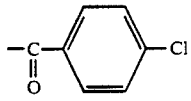 | 4-Cl—$C_6H_4$ | Cl | N | Resin |
| 109 | 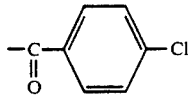 | 2,4-$Cl_2$—$C_6H_3$ | Cl | N | |
| 110 | 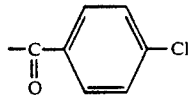 | 2-F—$C_6H_4$ | Cl | N | |
| 111 | 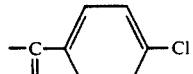 | 4-F—$C_6H_4$ | Cl | N | |
| 112 | 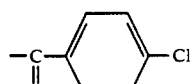 | 4-$CH_3$—$C_6H_4$ | Cl | N | |
| 113 | 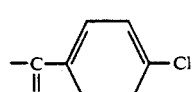 | 4-$CF_3$—$C_6H_4$ | Cl | N | |
| 114 |  | 3-Pyridyl | Cl | N | |
| 115 | 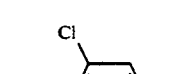 | 2-Furyl | Cl | N | |
| 116 | 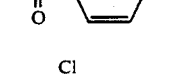 | $CH_3$ | Cl | N | |
| 117 |  | Cyclohexyl | Cl | N | |

TABLE-continued
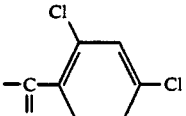
| Ex. | A | R | D | X | M.p./IR |
|---|---|---|---|---|---|
| 118 | 2,4-Cl₂-C₆H₃-C(O)- | C₆H₅ | Cl | N | |
| 119 | 2,4-Cl₂-C₆H₃-C(O)- | 2-Cl—C₆H₄ | Cl | N | |
| 120 | 2,4-Cl₂-C₆H₃-C(O)- | 4-Cl—C₆H₄ | Cl | N | |
| 121 | 2,4-Cl₂-C₆H₃-C(O)- | 2,4-Cl₂—C₆H₃ | Cl | N | |
| 122 | 2,4-Cl₂-C₆H₃-C(O)- | 2-F—C₆H₄ | Cl | N | |
| 123 | 2,4-Cl₂-C₆H₃-C(O)- | 4-F—C₆H₄ | Cl | N | |
| 124 | 4-F-C₆H₄-C(O)- | CH₃ | Cl | N | |
| 125 | 4-F-C₆H₄-C(O)- | C₃H₇ | Cl | N | |
| 126 | 4-F-C₆H₄-C(O)- | C₄H₉ | Cl | N | |
| 127 | 4-F-C₆H₄-C(O)- | Cyclohexyl | Cl | N | |
| 128 | 4-F-C₆H₄-C(O)- | C₆H₅ | Cl | N | |

TABLE-continued
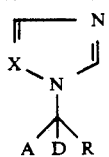
| Ex. | A | R | D | X | M.p./IR |
|---|---|---|---|---|---|
| 129 | -C(=O)-C6H4-4-F | 2-Cl—C6H4 | Cl | N | |
| 130 | -C(=O)-C6H4-4-F | 4-Cl—C6H4 | Cl | N | |
| 131 | -C(=O)-C6H4-4-F | 2,4-Cl2—C6H3 | Cl | N | |
| 132 | -C(=O)-C6H4-4-F | 2-F—C6H4 | Cl | N | |
| 133 | -C(=O)-C6H4-4-F | 4-F—C6H4 | Cl | N | 1701, 1598, 1508, 1237, 1161 cm$^{-1}$ |
| 134 | -C(=O)-C6H4-4-F | 2-Br—C6H4 | Cl | N | |
| 135 | -C(=O)-C6H4-4-F | 4-Br—C6H4 | Cl | N | |
| 136 | -C(=O)-C6H4-4-F | 2-CH3—C6H4 | Cl | N | |
| 137 | -C(=O)-C6H4-4-F | 4-CH3—C6H4 | Cl | N | |
| 138 | -C(=O)-C6H4-4-F | 2-CF3—C6H4 | Cl | N | |
| 139 | -C(=O)-C6H4-4-F | 4-CF3—C6H4 | Cl | N | |
| 140 | -C(=O)-C6H4-4-F | 1-Naphthyl | Cl | N | |

TABLE-continued
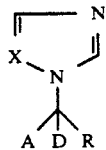
| Ex. | A | R | D | X | M.p./IR |
|---|---|---|---|---|---|
| 141 | -C(=O)-C₆H₄-F (4-F) | 2-Naphthyl | Cl | N | |
| 142 | -C(=O)-C₆H₄-F (4-F) | 4-Biphenylyl | Cl | N | |
| 143 | -C(=O)-C₆H₄-F (4-F) | 2-Furyl | Cl | N | |
| 144 | -C(=O)-C₆H₄-F (4-F) | 2-Thienyl | Cl | N | |
| 145 | -C(=O)-C₆H₄-F (4-F) | 3-Pyridyl | Cl | N | |
| 146 | -C(=O)-C₆H₄-CH₃ (4-CH₃) | CH₃ | Cl | N | |
| 147 | -C(=O)-C₆H₄-CH₃ (4-CH₃) | Cyclohexyl | Cl | N | |
| 148 | -C(=O)-C₆H₄-CH₃ (4-CH₃) | C₆H₅ | Cl | N | |
| 149 | -C(=O)-C₆H₄-CH₃ (4-CH₃) | 2-Cl—C₆H₄ | Cl | N | |
| 150 | -C(=O)-C₆H₄-CH₃ (4-CH₃) | 4-Cl—C₆H₄ | Cl | N | |
| 151 | -C(=O)-C₆H₄-CH₃ (4-CH₃) | 2,4-Cl₂—C₆H₃ | Cl | N | |
| 152 | -C(=O)-C₆H₄-CH₃ (4-CH₃) | 2-F—C₆H₄ | Cl | N | |

TABLE-continued

| Ex. | A | R | D | X | M.p./IR |
|---|---|---|---|---|---|
| 153 | -C(=O)-C6H4-4-CH3 | 4-F—C6H4 | Cl | N | |
| 154 | -C(=O)-C6H4-4-CH3 | 4-CH3—C6H4 | Cl | N | |
| 155 | -C(=O)-C6H4-4-CH3 | 4-CF3—C6H4 | Cl | N | |
| 156 | -C(=O)-C6H4-4-OCH3 | CH3 | Cl | N | |
| 157 | -C(=O)-C6H4-4-OCH3 | Cyclohexyl | Cl | N | |
| 158 | -C(=O)-C6H4-4-OCH3 | 4-Cl—C6H4 | Cl | N | |
| 159 | -C(=O)-C6H4-4-OCH3 | 4-F—C6H4 | Cl | N | |
| 160 | -C(=O)-C6H4-4-OCH3 | 4-OCH3—C6H4 | Cl | N | |
| 161 | -C(=O)-C6H4-4-CF3 | CH3 | Cl | N | |
| 162 | -C(=O)-C6H4-4-CF3 | C3H7 | Cl | N | |
| 163 | -C(=O)-C6H4-4-CF3 | Cyclohexyl | Cl | N | |
| 164 | -C(=O)-C6H4-4-CF3 | 2-Cl—C6H4 | Cl | N | |

TABLE-continued
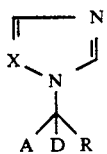
| Ex. | A | R | D | X | M.p./IR |
|---|---|---|---|---|---|
| 165 | -C(=O)-C6H4-CF3 (4-) | 4-Cl—C6H4 | Cl | N | |
| 166 | -C(=O)-C6H4-CF3 (4-) | 2,4-Cl2—C6H3 | Cl | N | |
| 167 | -C(=O)-C6H4-CF3 (4-) | 4-F—C6H4 | Cl | N | |
| 168 | -C(=O)-C6H4-CF3 (4-) | 4-CH3—C6H4 | Cl | N | |
| 169 | -C(=O)-C6H4-CF3 (4-) | 4-CF3—C6H4 | Cl | N | |
| 170 | -C(=O)-CH3 | CH3 | Cl | N | |
| 171 | -C(=O)-CH3 | Cyclohexyl | Cl | N | |
| 172 | -C(=O)-CH3 | C6H5 | Cl | N | |
| 173 | -C(=O)-CH3 | 2-Cl—C6H4 | Cl | N | |
| 174 | -C(=O)-CH3 | 4-Cl—C6H4 | Cl | N | |
| 175 | -C(=O)-CH3 | 2,4-Cl2—C6H3 | Cl | N | |
| 176 | -C(=O)-CH3 | 2-F—C6H4 | Cl | N | |
| 177 | -C(=O)-CH3 | 4-F—C6H4 | Cl | N | |
| 178 | -C(=O)-CH3 | 4-CH3—C6H4 | Cl | N | |
| 179 | -C(=O)-CH3 | 4-CF3—C6H4 | Cl | N | |

TABLE-continued

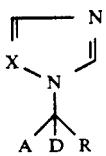

| Ex. | A | R | D | X | M.p./IR |
|---|---|---|---|---|---|
| 180 | —C(=O)—CH₃ | 3-Pyridyl | Cl | N | |
| 181 | —C(=O)—CH₃ | 2-Thienyl | Cl | N | |
| 182 | —C(=O)—C₃H₇ | CH₃ | Cl | N | |
| 183 | —C(=O)—C₃H₇ | Cyclohexyl | Cl | N | |
| 184 | —C(=O)—C₃H₇ | C₆H₅ | Cl | N | |
| 185 | —C(=O)—C₃H₇ | 2-Cl—C₆H₄ | Cl | N | |
| 186 | —C(=O)—C₃H₇ | 4-Cl—C₆H₄ | Cl | N | |
| 187 | —C(=O)—C₃H₇ | 2,4-Cl₂—C₆H₃ | Cl | N | |
| 188 | —C(=O)—C₃H₇ | 2-F—C₆H₄ | Cl | N | |
| 189 | —C(=O)—C₃H₇ | 4-F—C₆H₄ | Cl | N | |
| 190 | —C(=O)—C₃H₇ | 4-CH₃—C₆H₄ | Cl | N | |
| 191 | —C(=O)—C₃H₇ | 4-CF₃—C₆H₄ | Cl | N | |
| 192 | Cyclohexyl | CH₃ | Cl | N | |
| 193 | Cyclohexyl | C₃H₇ | Cl | N | |
| 194 | Cyclohexyl | 2-Cl—C₆H₄ | Cl | N | |
| 195 | Cyclohexyl | 4-Cl—C₆H₄ | Cl | N | |
| 196 | Cyclohexyl | 4-F—C₆H₄ | Cl | N | |
| 197 | Cyclohexyl | 4-CH₃—C₆H₄ | Cl | N | |
| 198 | Cyclohexyl | Cyclohexyl | Cl | N | |

The novel compounds are suitable as fungicides.

The fungicidal compounds or the agents containing them can be applied, for example, in the form of directly sprayable solutions, powders, suspensions, including high-percentage aqueous, oily or other suspensions or dispersions, emulsions, oil dispersions, pastes, dusting or broadcasting agents or granules by spraying, atomizing, dusting, broadcasting or watering. The application forms depend on the purposes for which they are used; they ought in every case to ensure the finest possible distribution of the active ingredients according to the invention.

Normally, the plants are sprayed or dusted with the active ingredients, or the seeds of the plants are treated with the active ingredients.

The formulations are prepared in a conventional manner, eg. by extending the active ingredient with solvents and/or carriers, if required using emulsifiers and dispersants, it also being possible to use other organic solvents when water is used as diluent. Suitable auxiliaries for this purpose are essentially: solvents such as aromatic compounds (eg. xylene), chlorinated aromatic compounds (eg. chlorobenzenes), paraffins (eg. petroleum oil fractions), alcohols (eg. methanol, butanol), ketones (eg. cyclohexanone), amines (eg. ethanolamine), dimethylformamide and water; carriers such as natural rock powders (eg. kaolins, aluminas, talc, chalk) and synthetic rock powders (eg. highly disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are the alkali metal, alkaline earth metal and ammonium salts of aromatic sulfonic acids, eg. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, products of the condensation of sulfonated naphthalene and its derivatives with formaldehyde, products of the condensation of naphthalene or naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin-sulfite waste liquors or methylcellulose.

Powders and dusting and broadcasting agents can be prepared by mixing or grinding the active substances together with a solid carrier.

Granules, eg. coated, impregnated or homogeneous granules, can be prepared by binding the active ingredients to solid carriers. Examples of solid carriers are mineral earths such as silica gel, silicic acids, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

Examples of formulations are:

I. a solution of 90 parts by weight of compound No. 1 and 10 parts by weight of N-methyl-α-pyrrolidone which is suitable for use in the form of very small drops;

II. a mixture of 20 parts by weight of compound No. 28, 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil. A fine dispersion of the solution in water is used;

III. an aqueous dispersion of 20 parts by weight of compound No. 6, 40 parts by weight of cyclohexanone, 30 parts by weight of isobutanol, 20 parts by weight of the adduct of 40 moles of ethylene oxide and 1 mole of castor oil;

IV. an aqueous dispersion of 20 parts by weight of compound No. 82, 25 parts by weight of cyclohexanol, 65 parts by weight of a mineral oil fraction of boiling point 210 to 280° C. and 10 parts by weight of the adduct of 40 moles of ethylene oxide and 1 mole of castor oil;

V. a mixture, ground in a hammer mill, of 80 parts by weight of compound No. 133, 3 parts by weight of sodium diisobutylnaphthalene-α-sulfonate, 10 parts by weight of the sodium salt of a ligninsulfonic acid from a sulfite waste liquor and 7 parts by weight of powdered silica gel. A fine dispersion of this mixture can be used for spraying;

VI. an intimate mixture of 3 parts by weight of compound No. 1 and 97 parts by weight of finely divided kaolin; this dusting agent contains 3% by weight of active ingredient;

VII. an intimate mixture of 30 parts by weight of compound No. 28, 92 parts by weight of powdered silica gel and 8 parts by weight of liquid paraffin which was sprayed onto the surface of this silica gel; this formulation confers good adhesion on the active ingredient;

VIII. a stable aqueous dispersion of 40 parts by weight of compound No. 61, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of compound No. 82, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a liquid paraffin.

The novel compounds have excellent activity on a wide spectrum of phytopathogenic fungi, especially from the classes of Ascomycetes and Basidiomycetes. Some of them have systemic activity and can be employed as leaf and soil fungicides.

They are particularly important for controlling a large number of fungi on various crops such as wheat, rye, barley, oats, rice, corn, grass, cotton, soybean, coffee, sugar cane, grapevines, fruit and ornamental plants and vegetables such as cucumbers, beans and pumpkins, as well as on the seeds of these plants.

The compounds are applied by treating the fungi or the seeds, plants or materials to be protected from fungal attack, or the soil, with a fungicidal amount of the active ingredients.

Application is carried out before or after infection of the materials, plants or seeds by the fungi.

The compounds I are specifically suitable for controlling the following plant diseases:

Erysiphe graminis (powdery mildew) in cereals,
Erysiphe cichoracearum and Sphaerotheca fuliginea on pumpkins,
Podosphaera leucotricha on apples,
Uncinula necator on grapevines,
Puccinia species on cereals,
Rhizoctonia species on cotton and lawns,
Ustilago species on cereals and sugar cane,
Venturia inaequalis (scab) on apples,
Helminthosporium species on cereals,
Septoria nodorum on wheat,
Botrytis cinerea (gray mold) on strawberries and grapevines,
Cercospora arachidicola on peanuts,
Pseudocercosporella herpotrichoides on wheat and barley,
Pyricularia oryzae on rice,
Phytophthora infestans on potatoes and tomatoes,
Fusarium and Verticillium species on various crops,
Plasmopara viticola on grapevines,
Alternaria species on fruit and vegetables.

The novel compounds can also be employed to protect materials (wood) eg. against Paecilomyces variotii.

The fungicidal agents generally contain from 0.1 to 95, preferably 0.5 to 90, % by weight of active ingredient.

The application rates depend on the nature of the desired effect and range from 0.02 to 3 kg of active ingredient per ha.

The amounts of active ingredient required for seed treatment are generally from 0.001 to 50 g, preferably 0.01 to 10 g, per kilogram of seeds.

The fungicidal agents according to the invention can also contain other active ingredients, eg. herbicides, insecticides, growth regulators, fungicides or even fertilizers. In many cases this admixture with the fungicides results in an extension of the spectrum of fungicidal action.

The following list of fungicides with which the novel compounds can be applied is intended to illustrate but not restrict the possible combinations:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and N,N'-propylenebis(thiocarbamoyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropyl carbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamoyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N,,N,-dimethyl-N-phenyl-sulfamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethylfuran-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl TM N-tridecylmorpholine and its salts,
2,6-dimethyl-N-cyclododecylmorpholine and its salts,
N-[3-(p-tert-butylphenyl)-2-methylpropyl]-cis-2,6-dimethylmorpholine,
N-[3-(p-tert-butylphenyl)-2-methylpropyl]-piperidine,
1-[2-(2,4-dichlorophenyl)-4-ethyl-1,3-dioxolan-2-yl-ethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidine-methanol,
5-butyl-2-dimethylamino-4-hydroxy-6-methylpyrimidine. bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
methyl DL-N-(2,6-dimethylphenyl)-N-fur-2-oylalanate,
methyl DL-N-(2,6-dimethylphenyl)-N-(2,-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use examples

The prior art compound used for comparison purposes was 1-chloro-1-(1,2,4-triazol-1-yl)-2-phenyl-3-(4-fluorophenyl)-propane (A) disclosed in EP 346,727.

Use Example 1

Action on wheat mildew

Leaves of pot-grown wheat seedlings of the "Kanzler" variety were sprayed with aqueous liquors containing (dry basis) 80% of active ingredient and 20% emulsifier, and dusted, 24 hours after the sprayed-on layer had dried, with spores of wheat mildew (Erysiphe graminis var. tritici). The plants were then set up in the greenhouse at from 20° to 22° C. and a relative humidity of from 75 to 80%. The extent of mildew spread was assessed after 7 days.

The results of this experiment show that active ingredients nos. 1, 28, 30 and 61, applied as aqueous dispersions containing 250 ppm of active ingredient, have a better fungicidal action (99%) than prior art comparative compound A (75%).

Use Example 2

Action on wheat brown rust

Leaves of pot-grown wheat seedlings of the "Kanzler" variety were dusted with spores of brown rust (Purrinia recondita). The pots were then placed for 24 hours at 20° to 22° C. in a high-humidity (90-95%) chamber. During this period the spores germinated and the gem tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results of this experiment show that active ingredients nos. 28 and 30, applied as aqueous dispersions containing 250 ppm of active ingredient, have a better fungicidal action (93%) than prior art comparative compound A (50%).

We claim:

1. A member selected from the group consisting of a 1-halo-1-azolylmethane derivative of the formula I

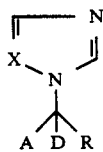

where
  A and R are identical or different and are each $C_1$-$C_8$-alkyl, $C_3$-$C_8$-cycloalkyl, benzyl, benzoyl, $C_1$-$C_8$-acyl, biphenylyl, naphthyl, or phenyl, it being possible for each of these radicals to be substituted one to three times by halogen, nitro, phenoxy, amino, $C_1$-$C_4$-alkyl, $C_1$-$C_4$-alkoxy or $C_1$-$C_4$-haloalkyl;
  D is Cl or Br, and
  X is N,
and the plant-compatible acid addition salts and metal complexes thereof.

2. A fungicidal composition containing an inert carrier and a fungicidally effective amount of a 1-halo-1-azolylmethane derivative of the formula I

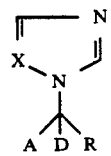

where
  A and R are identical or different and are each $C_1$-$C_8$-alkyl, $C_3$-$C_8$-cycloalkyl, benzyl, benzoyl, $C_1$-$C_8$-acyl, biphenylyl, naphthyl, or phenyl, it being possible for each of these radicals to be substituted one to three times by halogen, nitro, phenoxy, amino, $C_1$-$C_4$-alkyl, $C_1$-$C_4$-alkoxy or $C_1$-$C_4$-haloalkyl;
  D is Cl or Br, and
  X is N,
or a plant-compatible salt or metal complex thereof.

3. A method for controlling fungi, which comprises contacting the fungi or the plants threatened by fungal attack, or their habitat, or materials, or seeds with a fungicidally effective amount of a 1-halo-1-azolylmethane derivative of the formula I

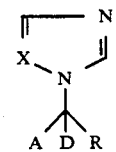

where
  A and R are identical or different and are each $C_1$-$C_8$-alkyl, $C_3$-$C_8$-cycloalkyl, benzyl, benzoyl, $C_1$-$C_8$-acyl, biphenylyl, naphthyl, or phenyl, it being possible for each of these radicals to be substituted one to three times by halogen, nitro, phenoxy, amino, $C_1$-$C_4$-alkyl, $C_1$-$C_4$-alkoxy or $C_1$-$C_4$-haloalkyl;
  D is Cl or Br, and
  X is N,
or a plant-compatible salt or metal complex thereof.

4. A compound of the formula I as claimed in claim 1, where A and R are each benzyl, and D is Cl.

5. A compound of the formula I as claimed in claim 1, where A and R are each 4-fluorobenzyl, and D is Cl.

6. A compound of the formula I as claimed in claim 1, where A is 2,4-dichlorobenzyl, R is butyl, and D is Cl.

7. A compound of the formula I as claimed in claim 1, where A is benzoyl, R is phenyl, and D is Cl.

8. A compound of the formula I as claimed in claim 1, where A is 4-fluorobenzoyl, R is 4-fluorophenyl, and D is Cl.

* * * * *